US006600805B2

United States Patent
Hansen

(10) Patent No.: US 6,600,805 B2
(45) Date of Patent: Jul. 29, 2003

(54) METHOD AND APPARATUS FOR DETERMINATION OF PROPERTIES OF FOOD OR FEED

(75) Inventor: Per Waaben Hansen, Lyngby (DK)

(73) Assignee: Foss Electric A/S, Hillerod (DK)

( * ) Notice: Subject to any disclaimer, the term of this patent is extended or adjusted under 35 U.S.C. 154(b) by 0 days.

(21) Appl. No.: 10/117,237

(22) Filed: Apr. 8, 2002

(65) Prior Publication Data
US 2002/0168046 A1 Nov. 14, 2002

Related U.S. Application Data

(63) Continuation of application No. PCT/DK00/00588, filed on Oct. 20, 2000.

(30) Foreign Application Priority Data

Oct. 21, 1999 (DK) .......................................... 1999 01512

(51) Int. Cl.⁷ ......................... G01N 23/083; H05G 1/64
(52) U.S. Cl. ....................... 378/53; 378/98.9; 378/207; 250/252.1; 702/172
(58) Field of Search .............................. 378/53, 54, 51, 378/98.9, 207; 250/252.1, 358.1, 359.1; 702/85, 101, 172–173

(56) References Cited

U.S. PATENT DOCUMENTS

| | | | | |
|---|---|---|---|---|
| 4,168,431 A | * | 9/1979 | Henriksen | 378/53 |
| 4,171,164 A | | 10/1979 | Groves et al. | |
| 4,504,963 A | * | 3/1985 | Johnson | 378/53 |
| 5,252,829 A | | 10/1993 | Nygaard et al. | |
| 5,428,657 A | | 6/1995 | Papanicolopoulos et al. | |
| 5,459,677 A | | 10/1995 | Kowalski et al. | |
| 5,585,603 A | | 12/1996 | Vogeley, Jr. | |
| 5,682,411 A | | 10/1997 | Rushbrooke et al. | |
| 5,841,833 A | * | 11/1998 | Mazess et al. | 378/146 |
| 6,173,038 B1 | * | 1/2001 | Siffert et al. | 378/54 |
| 6,233,473 B1 | * | 5/2001 | Shepherd et al. | 378/54 |

(List continued on next page.)

FOREIGN PATENT DOCUMENTS

| | | |
|---|---|---|
| DE | 44 06 958 A1 | 9/1995 |
| DK | 172377 B1 | 4/1998 |
| SE | 92/03711 | 12/1992 |
| WO | WO 92/05703 | 4/1992 |
| WO | WO 93/06460 | 4/1993 |
| WO | WO 95/16201 | 6/1995 |
| WO | WO 98/43070 | 10/1998 |

OTHER PUBLICATIONS

Elowsson, Per et al., "An evaluation of Dual–Energy X–ray Absorptiometry and Underwater Weighing to Estimate Body Composition by Means of Carcass Analysis in Piglets," J Nutr., Sep. 1998, vol. 128, Iss. 9, pp. 1543–1549.*

(List continued on next page.)

Primary Examiner—Drew A. Dunn
(74) Attorney, Agent, or Firm—Birch, Stewart, Kolasch & Birch, LLP

(57) ABSTRACT

Properties of a medium of food or feed, such as the fat content of meat, are determined by the use of dual X-ray absorptiometry with dual energy levels. Substantially, the entire medium is scanned by X-ray beams, and the X-rays passing through the medium are detected for a plurality of areas (pixels) of the medium. For each area, values $A_{low}$ and $A_{high}$, representing absorption in the area of the medium at low and high energy levels are calculated. A plurality of values being products of the type $A_{low}^{n} * A_{high}^{m}$ are generated and used for predicting the properties of the medium in this area. Thereby the accuracy of the property determination is improved considerably.

27 Claims, 13 Drawing Sheets

U.S. PATENT DOCUMENTS 6,285,740 B1 * 9/2001 Seely et al. ................ 378/98.8
6,370,223 B1 * 4/2002 Gleason et al. ............... 378/58
6,385,284 B1 * 5/2002 Parmee ....................... 378/54

OTHER PUBLICATIONS

Bertin, Eric et al., "Evaluation of Dual–Energy Absorptiomettry for Body–Compostion Assessment in Rats," J Nutr., Sep. 1998, vol. 128, Iss 9, pp. 1550–1554.*

Haarbo, J. et al., "Validation of body composition by dual energy X–ray absoptiometry (DEXA)", Clinical Physiology (1991), vol. 11, pp. 331–341.

Mitchell, A.D. et al., "Composition Analysis of Beef Rib Sections by Dual–energy X–ray Absorptiometry", Meat Science (1997), vol. 47, No. 1/2, pp 115–124.

Mitchell, A.D. et al., "Composition Analysis of Pork Carcasses by Dual–Energy X–Ray Absorptiometry", J. Anim. Sci. (1998), vol. 76, pp. 2104–2114.

Svendsen, O.L. et al., "Accuracy of measurements of body composition by dual–energy x–ray absorptiometry in vivo", Am. J. Clin. Nutr. (1993), vol. 57, pp. 605–608.

* cited by examiner

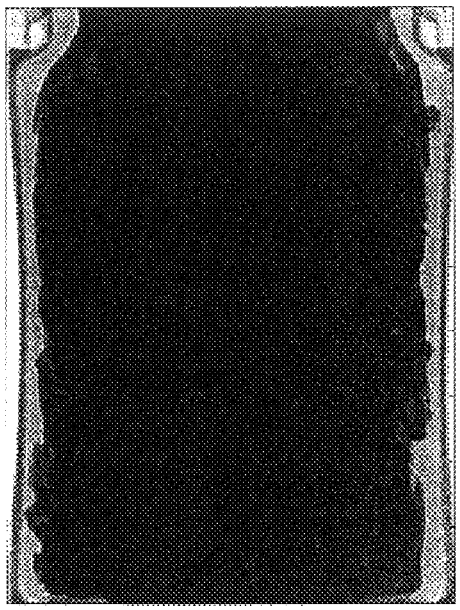
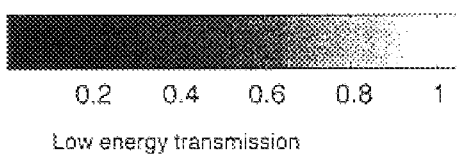
0.2  0.4  0.6  0.8  1
Low energy transmission
*Fig. 13*
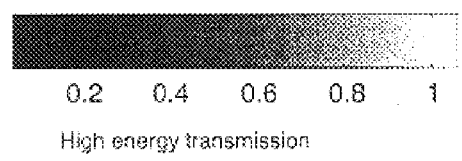
0.2  0.4  0.6  0.8  1
High energy transmission
*Fig. 14*

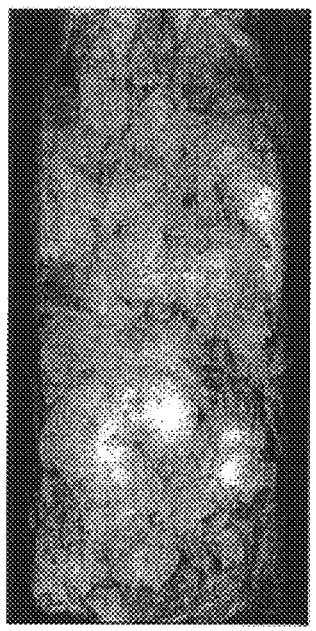
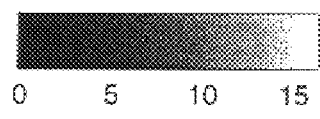
Areal density (g/cm²)
*Fig. 15*
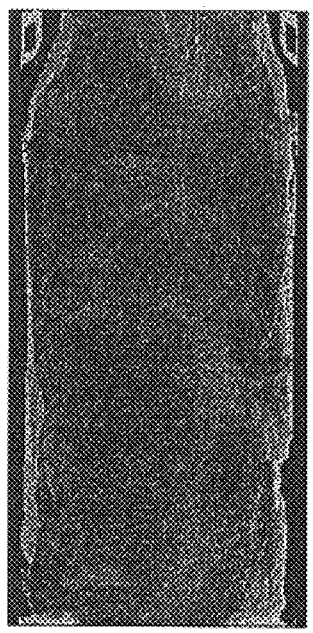
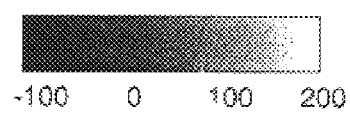
Fat content (%)
*Fig. 16*
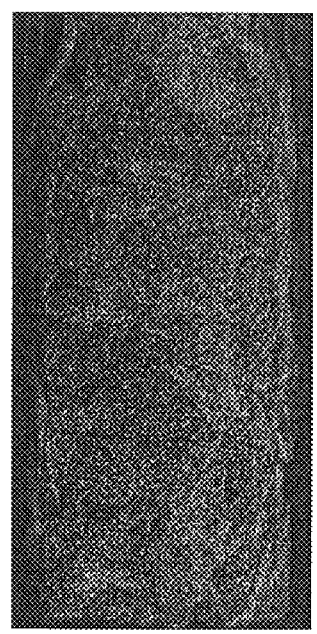
"Fat map" (g/cm²)
*Fig. 17*

US 6,600,805 B2

METHOD AND APPARATUS FOR DETERMINATION OF PROPERTIES OF FOOD OR FEED

This application is a continuation of PCT International Application No. PCT/DK00/00588 filed Oct. 20, 2000.

TECHNICAL FIELD

The present invention relates to X-ray analysis, and more specifically to the determination of properties of food or feed, such as the fat content of meat.

BACKGROUND ART

X-ray analysis for determining the fat content of meat has been known for several years. Such examples are described in numerous documents. U.S. Pat. No. 4,168,431 (Henriksen) discloses a multiple-level X-ray analysis for determining fat percentage. The apparatus includes at least three X-ray beams at different energy levels. DK PS 172 377 B1 discloses detection means for X-rays as well as a system for determination of properties of an item by use of X-rays. The system operates at a single energy level and applies two detection means separated by a X-ray attenuating material. WO 92/05703 discloses a method and device for cutting food products. The positioning of suitable cuts are guided by use of X-ray scanning showing the distribution of tissue type in the product. U.S. Pat. No. 5,585,603 discloses a method and system for weighing objects using X-rays. A continuous X-ray analysis for a meat blending system is known from U.S. Pat. No. 4,171,164 (Groves et al).

The percentages of fat in two meat streams are determined by passing a beam of polychromatic X-rays through the streams, measuring both the incident and the attenuated beams. U.S. Pat. No. 4,504,963 discloses an apparatus, system and method for determining the percentage of fat in a meat sample through use of X-ray radiation techniques. An automatic calibration is obtained by use of three incident beams, all at same energy level. Validation of body composition by dual energy X-ray absorptiometry is described in Clinical Physiology (1991) 11, 331–341. (J. Haarbo, A. Gotfredsen, C. Hassager and C. Christiansen). Further studies on bodies are reported in Am. J. Clinical Nutrition 1993: 57:605–608. (Ole Lander Svendsen, Jens Haarbo, Christian Hassager, and Claus Christiansen).

Recently analysis of meat has been reported in Meat Science Vol. 47, No 1/2, 115–124, 1997 (A. D. Mitchell, M. B. Solomon & T. S. Rumsey). A thorough study on pork carcasses by use of dual-energy X-ray absorptiometry was reported by P Elowsson et al (1998) J. Nutr. 128 1543–1549 An Evaluation of Dual-Energy X-Ray Absorptiometry and Underwater Weighing to estimate Body Composition by means of carcass Analysis in Piglets. (p. 1543, l.&r. col.; p. 1544, l.col.; p. 1547, l. col.). Another analysis on pork carcasses is reported by Mitchell et al., J. Anim. Sci. (1998), vol. 76, pp 2104–2113. However, on page 2113 of this analysis it is specifically concluded that the X-ray analysis is too slow for compatibility with on-line processing. None of the above-mentioned prior art has so far lead to an efficient apparatus fulfilling the needs in a slaughterhouse. Generally the prior art shows difficulties when measuring layers of varying thickness, specifically thin layers adjacent to thick layers. Further the prior art is unable to measure and provide results as fast as required to be useful for online processing.

The presently applied apparatus in most slaughterhouses is a Continuous Fat Analyser (Wolfking A/S, Denmark) and Infratec 1265 (Foss Tecator AB, Sweden) using NIR technology. Also applied is Anyl-Ray (The Kartridg Pak Co., Iowa) using a single energy X-ray on a sample of well-defined weight or volume.

It is an object of the present invention to provide a method and apparatus enabling a faster and more accurate determination than hitherto known, of the fat content in a food or feed product, such as a batch of meat trimmings, allowing creation of specific products (such as sausages or minced meat) having a desired content of fat, which is much more accurate than presently possible.

The present invention also applies regression analysis and multivariate calibration. Such analysis is known from e.g. the applicant's own WO 95/16201 disclosing the Determination of extraneous water in milk samples using regression analysis and multivariate calibration. Further, the applicant's WO 98/43070 discloses Measurement of acetone in milk using IR spectroscopy and multivariate calibration. U.S. Pat. No. 5,459,677 discloses a calibration transfer for analytical instruments. The applicant's WO 93/06460 discloses an infrared attenuation measuring system, including data processing based on multivariate calibration techniques, and the applicant's U.S. Pat. No. 5,252,829 discloses a determination of urea in milk with improved accuracy using at least part of an infrared spectrum.

DISCLOSURE OF THE INVENTION

The present invention relates to a method of determining properties a medium of food or feed, such as the fat content of meat, by use of dual X-ray absorptiometry, the medium being a raw material of food or feed, a product or intermediary product of food or feed, or a batch, sample or section of the same, the method comprising—scanning substantially all of the medium by X-ray beams having at least two energy levels, including a low level and a high level,—detecting the X-ray beams having passed through the medium for a plurality of areas (pixels) of the medium,—for each area calculating a value, $A_{low}$, representing the absorbance in the area of the medium at the low energy level,—for each area calculating a value, $A_{high}$ representing the absorbance in the area of the medium at the high energy level, characterised by for each area generating a plurality of values being products of the type $A_{low}^{n}*A_{high}^{m}$ wherein n and m are positive and/or negative integers or zero, and predicting the properties of the medium in this area by applying a calibration model to the plurality of values, wherein the calibration model defines relations between the plurality of values and properties of the medium.

The advantage over the prior art is a more accurate determination of the properties, such as the fat content in the medium. The accuracy is specifically improved over the prior art when measuring layers of varying thickness. A further advantage is due to the fact that using the method according to the invention almost the whole product is measured instead of a sampling. Generally, when using sampling in an inhomogeneous medium the extraction of a sample will introduce an error, because the sample may not be representative.

Preferably the plurality of values includes values $A_{low}^{n1}/A_{high}^{m1}$, wherein n1 and m1 are positive integers. Further on it is preferred that the plurality of values includes the values $A_{low}, A_{high}, A_{low}^{2}, A_{high}^{2}$, and $A_{low}/A_{high}$ and/or at least one of the values $A_{low}*A_{high}; A_{low}^{2}*A_{high}; A_{low}*A_{high}^{2}$ and/or at least one of the values $A_{low}*A_{high}; A_{low}^{2}*A_{high}; A_{low}*A_{high}^{2}; A_{low}*A_{high}^{4}$ and $A_{low}^{2}*A_{high}^{4}$ and/or at least one of the values $A_{low}^{2}/A_{high}; A_{low}/A_{high}^{2}$ and $A_{low}^{2}/A_{high}^{2}$;

$A_{low}^3/A_{high}^2$; $A_{low}^4/A_{high}^2$; $1/A_{high}^4$; $A_{low}^4/A_{high}^3$; $A_{low}^3/A_{high}^4$ and $A_{low}^4/A_{high}^4$.

Practical experiments have proved that such values contribute considerably to improve the accuracy.

Preferably the calibration model is obtained by use of a regression method being included in the group comprising Principal Component Regression (PCR), Multiple Linear Regression (MLR), Partial Least Squares (PLS) regression, and Artificial Neural Networks (ANN).

The present invention further relates to an apparatus for the determination of properties of a medium, such as the content of a component in the medium, the medium comprising a raw material of food or feed, a product or intermediary product of food or feed, or a batch, sample or section of the same, the apparatus comprising means (12, 14) for emitting at least two X-ray beams (16, 18) at two different energy levels, means for directing the at least two X-ray beams towards and through the medium, X-ray detection means (22, 24) covering a plurality of areas for detecting the two beams (16, 18) after passing through the medium, means (27, 28, 34, 35) for transferring and converting output signals from the detection means (22, 24) into digital data set for input to data processing means (38) for receiving, storing and processing the at least two data set representing X-ray images at the at least two different energy levels, the apparatus further comprising means for synchronising the at least two data sets and the data processing means including means for calculating values representing the absorbances ($A_{low}$, $A_{high}$) in each area of the medium at the at least two energy levels, characterised in that the data processing means comprise means for generating a plurality of values being products of the type $A_{low}^{n}*A_{high}^{m}$ wherein n and m are positive and/or negative integers or zero, and means for predicting the properties of the medium in this area by applying a calibration model to the plurality of values, wherein the calibration model defines relations between the plurality of values and properties of the medium.

The advantage over the prior art is a faster and more accurate determination, which is so fast that it can be applied continuously on a process line in a slaughterhouse. The medium is arranged on a conveyor moving at substantially constant speed, and the at least two X-ray beams are fan-shaped, and the low level beam is detected by a first linear array, being dedicated to the detection of the low energy beam, and the high level beam is detected by a second linear array being dedicated to the detection of the high energy beam, each comprising a plurality of pixels.

The apparatus may be characterised by comprising at least one low energy X-ray source (12) arranged above the medium (20) for providing a fan-shaped low energy beam (16) substantially covering the width of medium and at least one high energy X-ray source (14) arranged above the medium (20) for providing a fan-shaped low energy beam (16) covering the width of medium (20) and a first X-ray detection means (22) arranged to be exposed to the fan-shaped low energy beam (16) and below the medium (20) a second X-ray detection means (24) arranged to be exposed to the fan-shaped high energy beam (18) and below the medium (20), and electronic means (34, 38, 42) including the data processing means (38) and communicating with the detectors (22, 24) and arranged to store and process data representing signals from the detection means (22, 24), and further comprising means (10) for moving the medium (20) relative to the X-ray beams (16, 18) or visa versa.

The apparatus may be characterised in that the data processing means include and/or communicate with means including data storage means comprising a calibration model prepared by use of multivariate calibration methods such as Artificial Neural Networks (ANN), or PCR, MLR or PLS regression analysis.

The apparatus may be characterised by comprising at least two sources (12, 14) emitting X-rays of two different energy levels.

The apparatus may be characterised by the two energy levels comprising a low energy level in a range between 35 and 75 keV, preferably between 45 and 70 key and most preferred about 62 key, and a high energy level in a range between about 60 and 140 keV, preferably between 80 and 130 key and most preferred about 120 keV.

The apparatus may be characterised by comprising filter means located in each of the beams (16, 18)

The apparatus may be characterised by comprising one X-ray source and two filter means splitting the beam into two beams of X-rays at two different energy levels.

The apparatus may be characterised in that the means (12, 14) for emitting at least two X-ray beams, the means for directing the at least two X-ray beams and the X-ray detection means (22, 24) are mutually fixed.

The apparatus may be characterised by comprising means (12, 14) for emitting spatially separated fan-shaped beams (16, 18).

The apparatus may be characterised in that the detection means (22,24) are covered by a scintillating layer, e.g. cadmium telluride, mercury iodide, and/or gadolinium oxysulphide.

The apparatus may be characterised by comprising conveyor means (10) arranged to carry container means (20), such as a tray or an open box, adapted to accommodate a random number of meat lumps of various sizes to be analysed, the conveyor means being arranged to let the container means (20) pass the at least two fan-shaped X-ray beams (16, 18).

The apparatus may be characterised by comprising conveyor means (10) wherein the conveyor belt is made from a material showing a low absorption of X-rays, and/or is split into two separate, spaced parts, the detector means (22, 24) being arranged in an open space between the two parts.

The apparatus may be characterised by comprising conveyor means (10) adapted to accommodate a Continuous flow of meat lumps of various sizes to be analysed, the conveyor means being arranged to let the meat lumps pass the at least two fan-shaped X-ray beams (16, 18).

The apparatus may be characterised by being arranged to perform the following steps: scan at least a section of a medium by X-ray beams having at least two energy levels, store data representing at least two X ray images of the medium, calculate the fat content and/or areal density for all points (pixels) obtained from the scanning by use of multivariate calibration models generated in a previously performed calibration step, multiply the fat content and areal density at each point, in order to generate a "fat map" (in $g/cm^2$) of the sample, add all points in the "fat map" to give the total fat weight ($F_{total}$) of the sample, add all areal densities for the sample to give the total weight ($W_{total}$) of the sample, calculate the average fat content of the sample as the ratio $F_{total}/W_{total}$.

The present invention further relates to a method for calibration of an apparatus comprising preparation of a plurality of calibration samples consisting of specified food or feed products, such as minced pork meat, of various well-defined heights and properties, measuring the plurality of calibration samples in the apparatus, thereby obtaining data representing two X-ray responses of each sample, each response comprising a plurality of pixels, and wherein the data of each pixel, or the mean of a number of neighbouring pixels, are processed using the formulas:

$$A_{low} = -\log_{10}\left[\frac{I_{sample}(\text{low}) - I_{dark}(\text{low})}{I_{air}(\text{low}) - I_{dark}(\text{low})}\right]$$

$$A_{high} = -\log_{10}\left[\frac{I_{sample}(\text{high}) - I_{dark}(\text{high})}{I_{air}(\text{high}) - I_{dark}(\text{high})}\right]$$

or similar expressions for calculation of values representing the absorbance in an area of the medium above a pixel or a number of neighbouring pixels, generating a plurality of values of the type $A_{low}^{n} * A_{high}^{m}$, wherein n and m are positive and/or negative integers and/or zero, correlating—by use of multivariate calibration methods, such as Artificial Neural Networks (ANN), or PCR, MLR or PLS regression—the data set for all/or a plurality of calibration samples to the properties determined by other means, such as a reference method,—in order to determine a number of calibration coefficients, providing a calibration model comprising the number of determined calibration coefficients.

All calibration samples are prepared in such a manner that they are homogeneous and of fixed areal densities, and further by averaging each of the values over all pixels at least in a defined portion of the images.

The invention further relates to a method of predicting the fat content of meat, comprising use of a calibration model obtained by a method. The invention also relates to an apparatus comprising a calibration model determined by a particular method.

By use of the present invention it is possible—more accurate and more rapidly than hitherto known—to determine the fat content of a random number of meat lumps (such as trimmings or cuts) of various sizes in a container (or similar means for enclosing or carrying a load of meat) or directly on a conveyor belt. The measurement may be performed within a fairly short time, such as a few seconds, e.g. about 4.5 or 9 seconds per container, each container having a volume of e.g. about 0.1 m³. Preferably, a smaller volume, about e.g. 25 kg meat, is arranged in each container. Accordingly, the method and apparatus may be applied for on-line control of the production of various meat products, such as minced meat, and more specifically where minced meat is produced from meat trimmings of various sizes.

According to the applicant's best knowledge multivariate calibration techniques have never been applied to X-ray analysis of meat, nor to X-ray analysis in general. The use of multivariate techniques solves a specific problem present when using the techniques according to the prior art. The known apparatus becomes highly inaccurate when measuring on a combination of thin and thick layers. When measuring meat lumps of various sizes the thickness of the layers through which the X-ray has to pass will vary considerably from 0 or almost 0 to a specified maximum. The use of a plurality of values allows a better accuracy of such measurements than hitherto known.

Further scope of the applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The present invention will become more fully understood from the detailed description given hereinbelow and the accompanying drawings which are given by way of illustration only, and thus are not limitative of the present invention, and wherein:

FIG. 13 shows a typical low energy X-ray transmission image of a meat sample as shown in FIG. 12.

FIG. 14 shows a typical high energy X-ray transmission image of the same meat sample.

FIG. 15 is an image illustrating a calculated areal density for each individual pixel.

FIG. 16 is an image illustrating a calculated fat content for each individual pixel.

FIG. 17 is an image illustrating a calculated "fat map" for a meat sample of 36% fat.

DETAILED DESCRIPTION OF A PREFERRED EMBODIMENT AND METHOD

Figure 1:
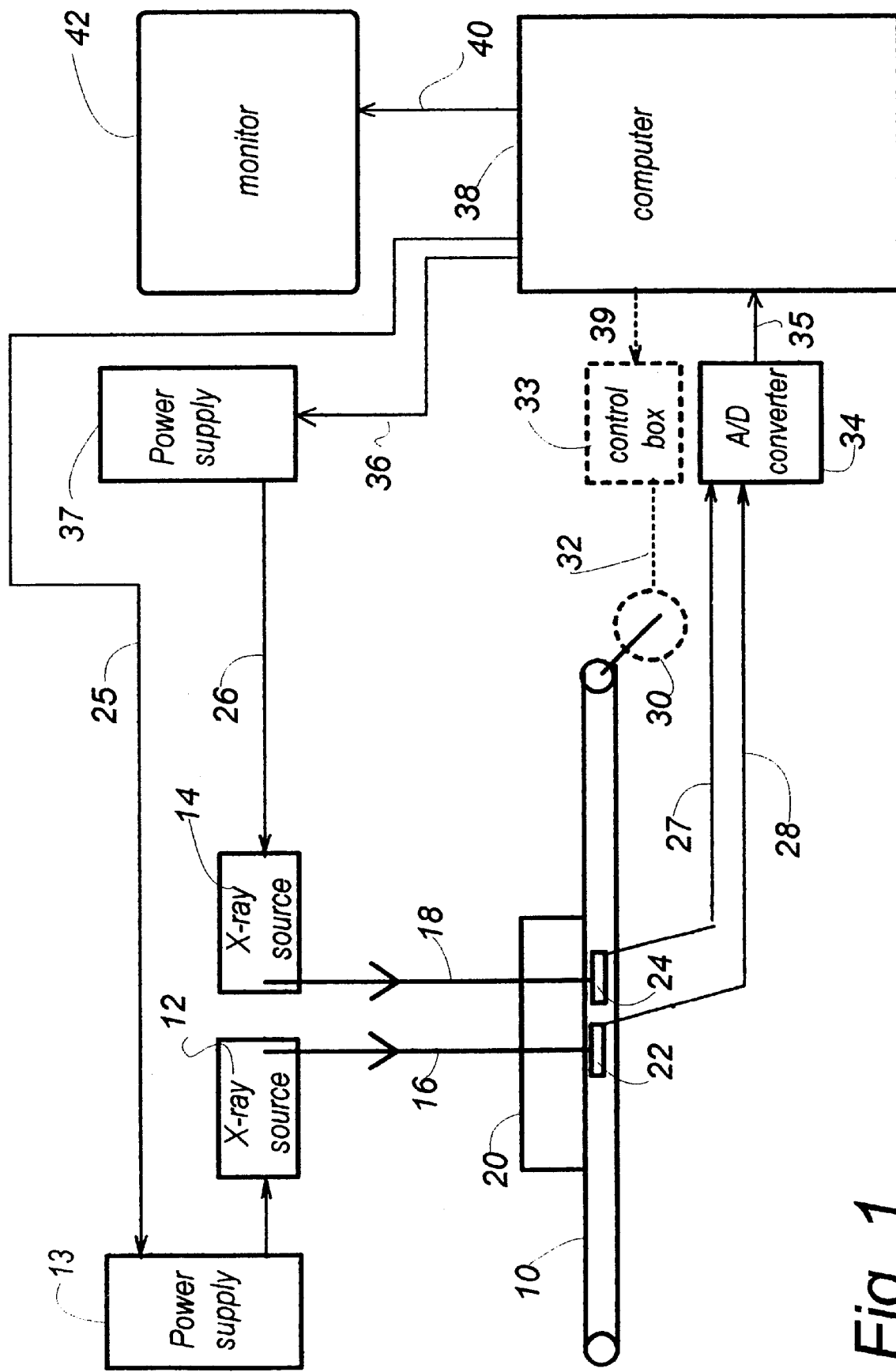
FIG. 1 shows as an example a system according to the invention
Figure 2:
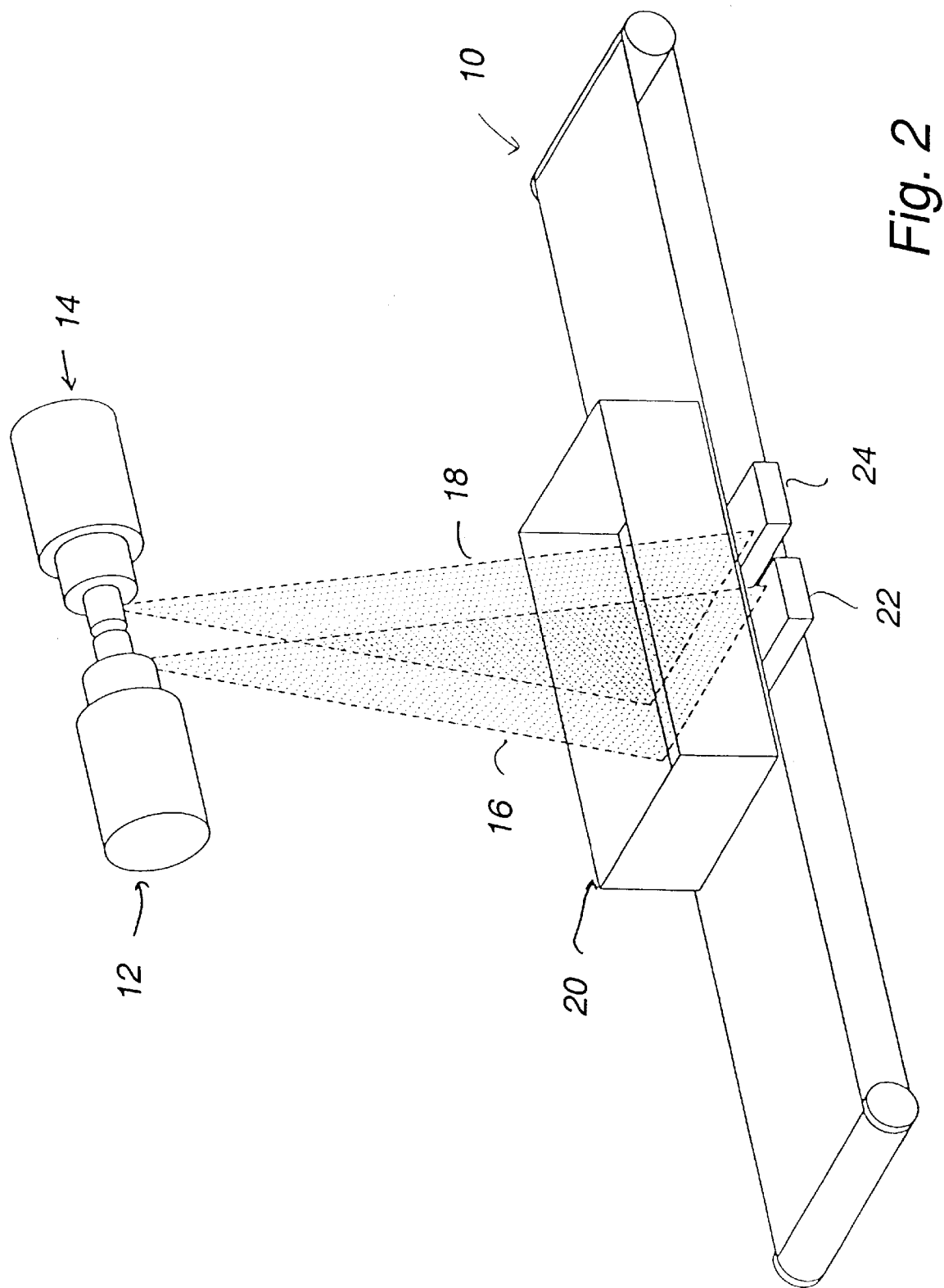
FIG. 2 shows a preferred embodiment of an X-ray apparatus according to the invention

The following description discloses as an example a preferred embodiment of the invention using two X-ray sources. The apparatus is designed for being installed in relation to a production line in a slaughterhouse. FIG. 1 shows a schematic diagram of an embodiment of a measurement system according to the invention. FIG. 2 illustrates the principle of the presently preferred X-ray apparatus. FIG. 2 shows only the active operating portions of the X-ray equipment. For purpose of clarity, all protective shielding or screening and all casings are deleted from the drawing. The equipment comprises or is located in close relation to a conveyor 10. Two X-ray sources 12, 14 are arranged above the conveyor 10. From the two sources 12, 14 X-ray beams 16, 18 are directed towards detectors 22, 24 arranged below the conveyor. The conveyor may be split into two separate conveyors spaced to allow free pass of the X-rays and to leave an open space for location of detectors 22, 24. Alternatively the conveyor belt should be made from a material showing a low absorbance of X-rays, e.g. polyurethane or polypropylene. The food or feed to be measured is arranged in an open container or box 20, preferably also composed by a material showing low absorbance of X-rays. Obviously in an alternative arrangement the sources could be located below the conveyor and the detectors above the conveyor.

The operational speed of the conveyor is preferably substantially constant. The items, motor 30, control box 33, and cables 32, 39, shown by phantom lines in FIG. 1, indicate that the operation of the conveyor optionally may be controlled by the computing means 38. The conveyor may include position measuring means, e.g. an encoder installed on a conveyor driving shaft. Alternative means may be a laser or radar detection or marks on the conveyor belt. It is essential to the present method that the data representing the two X-ray images can be synchronised. Such synchronisation may however be obtained in many ways, including mathematical post-processing of the images.

The equipment used in the present example consists of two constant potential X-ray sources 12, 14, one at low energy (e.g. 62 kV/5 mA) and another at high energy (e.g. 120 kV/3 mA), both with an appropriate filtration (e.g. using 0.25 and 1.75 mm of copper, respectively) narrowing the spectral range of the radiation emitted from the polychromatic sources. The two sources are spatially separated to avoid interference between them, i.e. to avoid that radiation from one source is detected as if it originated from the other. The radiation from either source is collimated by a lead collimator. In this way two fan-shaped beams of X-rays 16, 18 are directed through container 20 comprising a sample or batch of the food or feed product towards detectors 22, 24, e.g. Hamamatsu C 7390. Alternatively the meat lumps may be arranged loosely on a conveyor band.

Figure 3:
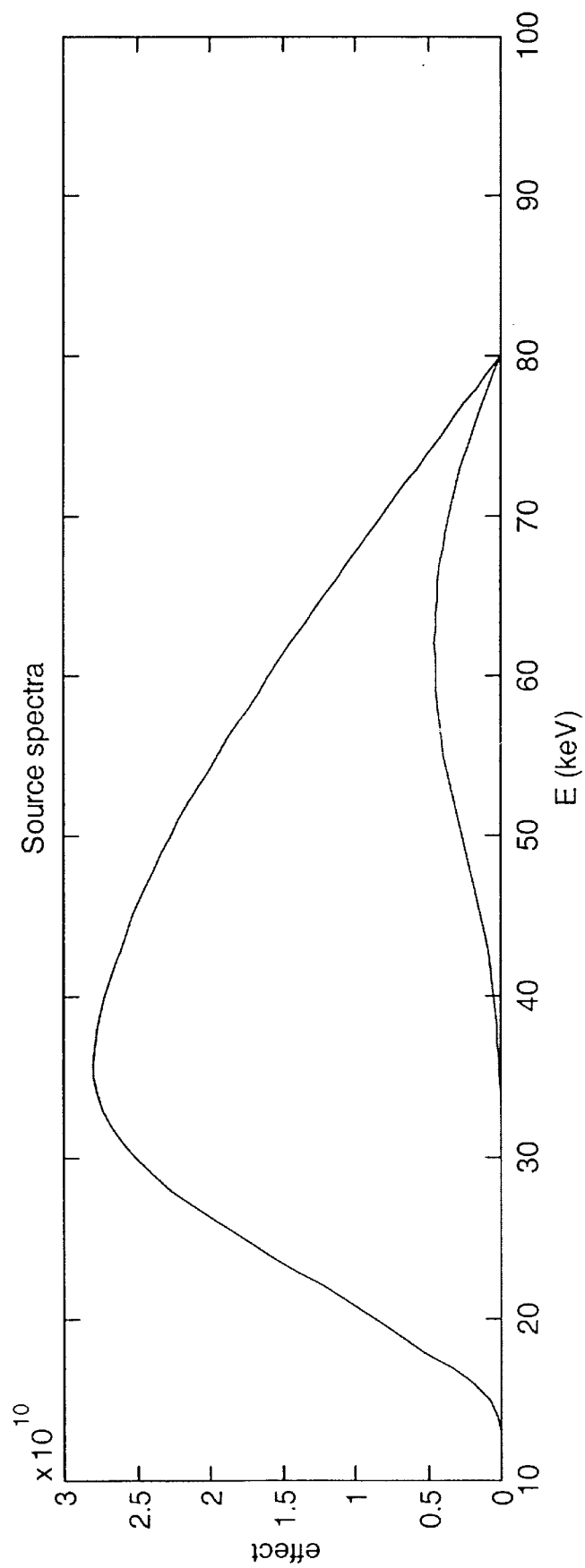
FIG. 3 shows a simulation of a system comprising one source and a combination of two filters.

Further, the two separate sources may be replaced by a combination of one source and two filters emitting a low energy and a high energy beam. The resulting source spectra are shown in FIG. 3. However the preferred embodiment applies two separate sources 12, 14 driven by separate power supplies 13, 37.

Both X-ray sources 12, 14 are associated with an array of detectors 22, 24 covered with a scintillating layer converting the transmitted radiation into visible light that can be measured by the detectors 22, 24. The scintillating layer may consist of e.g. cadmium telluride, mercury iodide, and/or gadolinium oxysulphide. The pixels used in the presently preferred embodiment have the dimensions 1.6×1.3 mm² and are arranged as an array of 384 pixels with a pitch of 1.6 mm. These dimensions are only stated as an example. Other dimensions may be applied. The pixels convert the amount of transmitted light into analogue signals that are passed through cables 27, 28 to an analogue-to-digital converter 34 which is connected through cable 35 to a computing means 38 capable of performing the successive calculations. A monitor 42 may be connected through cable 40 to the computing means to show results or details of the operation. The computing means 38 may include means for controlling the supply of power through means 36, 37, 26 and 25, 13, 15 to the X ray sources 12, 14. The monitor 42 and the computing means 38 may comprise a Personal Computer, preferably including at least one Pentium processor and/or a number of digital signal processors.

Operation

A container 20, comprising e.g. meat trimmings from a cutting section of the slaughterhouse, is received on the conveyor 10. The container is moved with a fairly constant speed of e.g. about 5–100 cm per second, such as 10–50 cm, e.g. 30 cm per second past the fan shaped beams 16, 18 and the arrays of detectors 22, 24 in a controlled manner in order to generate two images of the sample or batch, one at a low X-ray energy and another at a high energy. All data representing the two images are stored in the computer 38.

Treatment of the Collected Data

Figure 11:
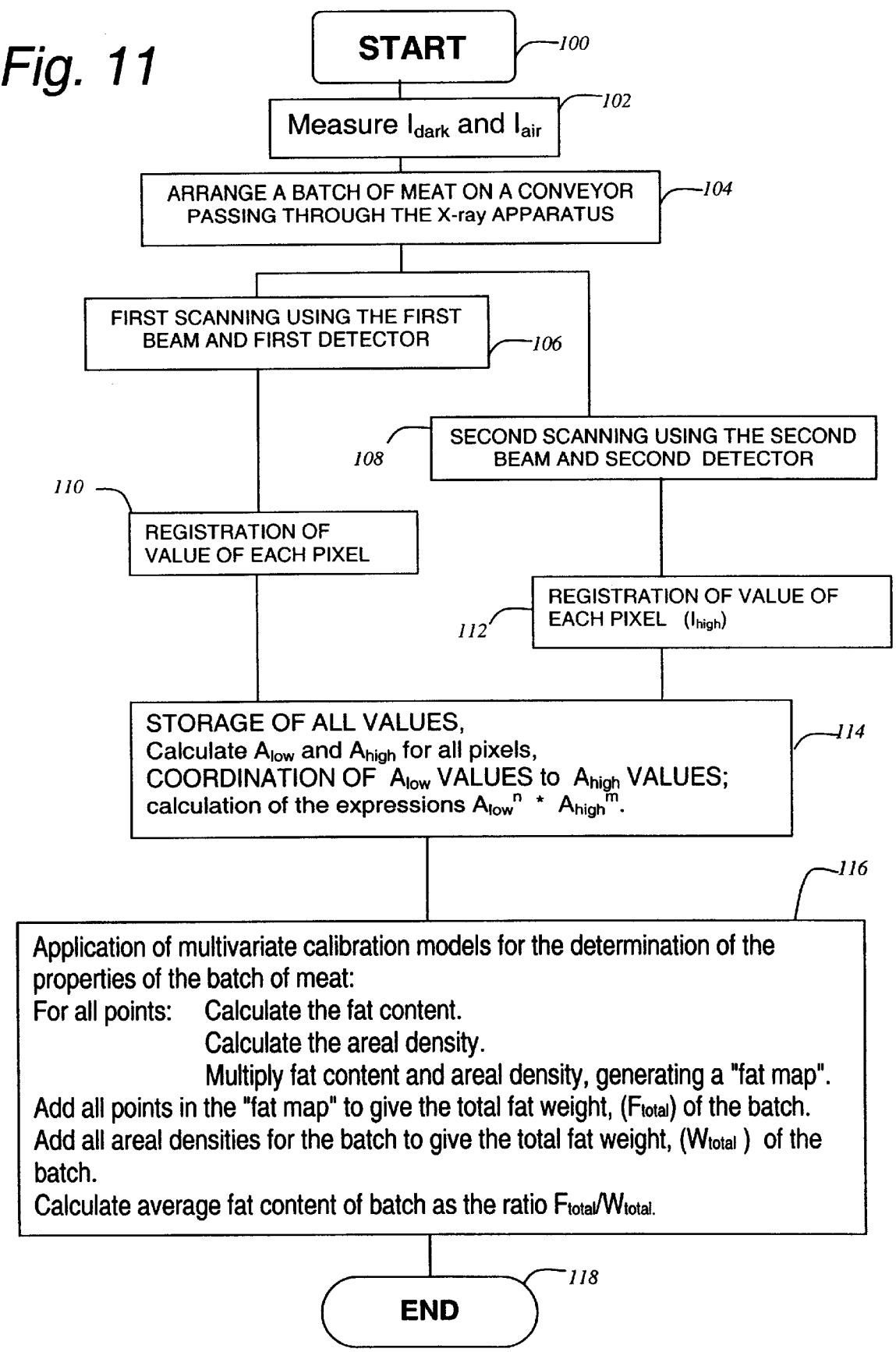
FIG. 11 shows a flow diagram illustrating the measuring process.

FIG. 11 represents a flow chart illustrating the measurement and data treatment. As stated above, two X-ray images of each container, comprising a batch of food or feed e.g. meat, are obtained. The signals at the pixels are $I_{low}$ and $I_{high}$ at low and high X-ray energies, respectively, (110, 112 in FIG. 11). Furthermore, the so-called "dark signals" (i.e. the signal from the detectors when no radiation reaches them), $I_{dark}(low)$ and $I_{dark}(high)$, and the "air signals" (i.e. the signal from the detectors when no sample is present in the sampling region), $I_{air}(low)$ and $I_{air}(high)$, are collected for each pixel at both X-ray energies (102 in FIG. 11). Preferably these data are collected repetitively in the intervals between the passage/passing of meat containers, i.e. the dark signals and air signals are measured repetitively, e.g. at regular intervals during a day to adjust for any drift of instrument performance.

Now referring to 114 in FIG. 11, these signals are transformed into absorbance units by using the following formulas:

$$A_{low} = -\log_{10}\left[\frac{I_{sample}(low) - I_{dark}(low)}{I_{air}(low) - I_{dark}(low)}\right]$$

$$A_{high} = -\log_{10}\left[\frac{I_{sample}(high) - I_{dark}(high)}{I_{air}(high) - I_{dark}(high)}\right]$$

From these two values, a plurality of values can be generated e.g.: $A_{low}$; $A_{high}$; $A_{low}^2$; $A_{high}^2$; $A_{low} \times A_{high}$; $A_{low}^2 \times A_{high}$; $A_{low} \times A_{high}^2$; $A_{low}/A_{high}$; $A_{low}^2/A_{high}$; $A_{low}/A_{high}^2$; $(A_{low}/A_{high})^2$;

or in a more generalised manner: $A_{low}^n * A_{high}^m$, wherein n and m are positive and/or negative integers and/or zero, These values are used as the input for the calibration routine establishing a relationship between the collected data and the component (e.g. the fat content) or the property (e.g. the areal density) of interest.

It is essential that a value $A_{low}$ for a specific pixel measuring the low energy transmittance through a specific area of the medium is matched to, the value $A_{high}$ for the pixel measuring the high energy transmission through exactly the same area of the medium. This can be accomplished by ensuring a synchronisation of the pictures as mentioned below.

If the low and high energy images are not perfectly aligned, i.e. if a specific region of the sample does not show up at exactly the same positions in the two images, large errors may result. This problem may occur e.g. if the two line scan detectors (22, 24) are not synchronised. A possible solution to this problem is to calculate the correlation between the two images using various shifts between them and thereby finding the shift at which the correlation is at a maximum, followed by a correction of one of the images by this shift. It is however preferred to synchronise the line scanning e.g. by the use of a position measuring means, or by tight control of the conveyor speed.

The following example explains how to generate a calibration model.

EXAMPLE

Calibration Against Fat Content and Areal Density

A set of 32 calibration samples consisting of minced pork meat were prepared. They were frozen in blocks of varying heights (5, 10, 15, and 20 cm) with horizontal dimensions of 10×10 $cm^2$. Their fat content (percentage) which ranged from 2.6 to 70.9%, were later determined by use of a wet chemistry method. The heights and fat contents (percentage), together with the fat-dependent density of meat, were used for calculating the areal densities of all 32 samples, ranging from 4.8 to 21.0 $g/cm^2$.

The frozen meat blocks were measured in the aforementioned X-ray equipment, yielding two images of each sample. The data points (pixels) of these images were treated according to the steps described above. To avoid random noise from influencing the calibration results, the 11 values generated from the original absorbance values were averaged over all pixels in the image. This could only be done since the samples were homogeneous and of fixed height.

This data set consisting of 11 variables obtained for all 32 samples was correlated against the fat content (percentage) measured by a reference method and the areal densities using the Partial Least Squares (PLS) regression method. This, and other similar multivariate calibration methods are well known (Martens and Næs: Multivariate Calibration, $2^{nd}$ ed., Wiley (1992)).

The calibrations were validated using full cross-validation, i.e. one sample at a time was removed from the data set for validation while the remaining 31 samples were used for calibration. This procedure was repeated for all samples, and validation results were generated by combining the validation results for all 32 samples.

Figure 4:
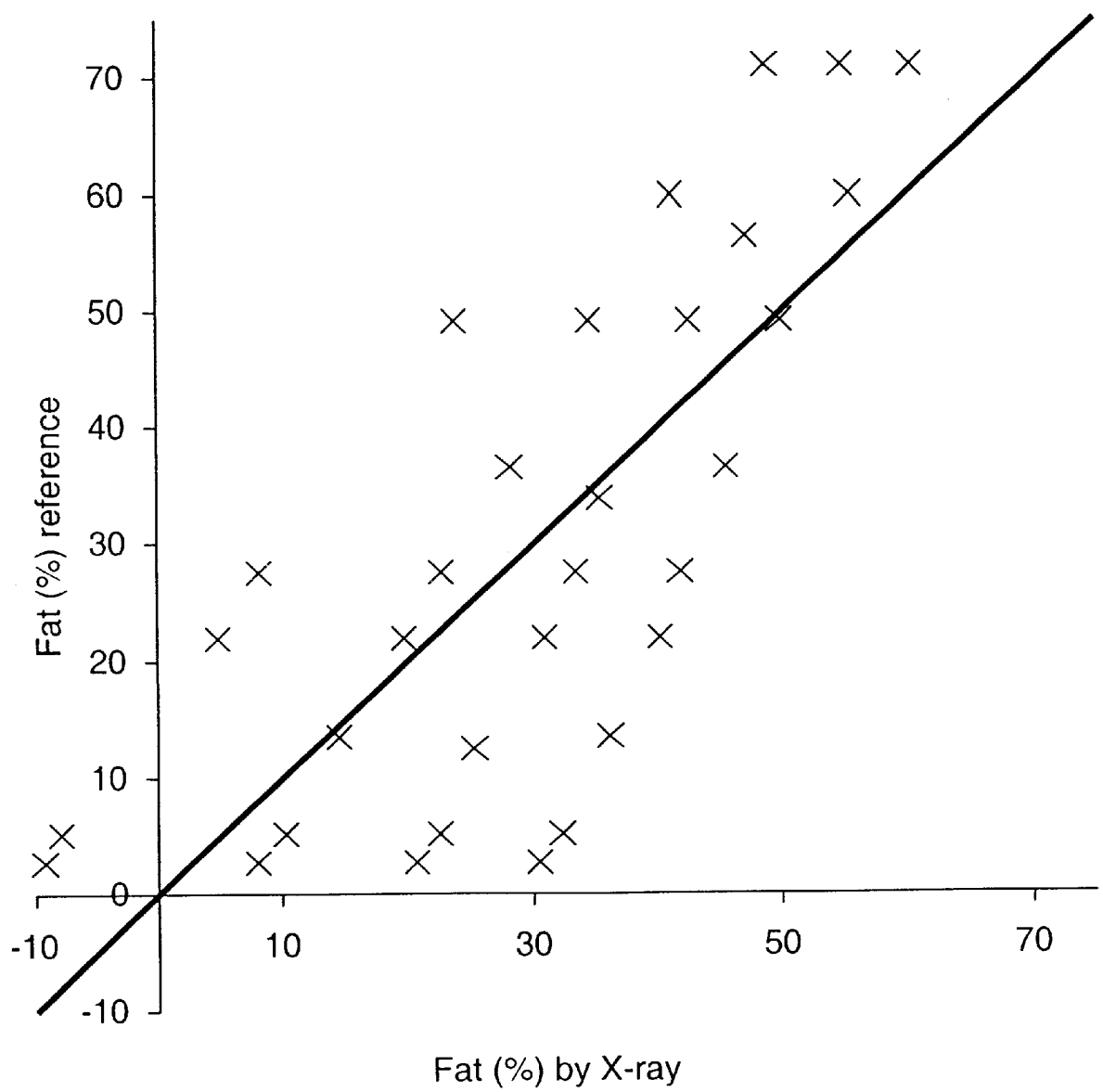
FIG. 4 shows cross-validated X-ray fat predictions versus reference fat content of 32 calibration samples when performing a simple univariate regression of $A_{low}/A_{high}$ against the reference fat content of the samples.

The traditional way of building an X-ray calibration model for fat in meat is by correlating the $A_{low}/A_{high}$ ratio to the fat reference results (Haardbo et al., Clin. Phys. (1991), vol. 11, pp. 331–341 or Mitchell et al. J. Anim. Sci. (1998), vol. 76, pp. 2104–2114). This method is, however, sensitive to the thickness (or areal density) of the sample and is therefore not useful with the range of sample heights (from 5 to 20 cm) of interest in the present context. This is evident from FIG. 4, where X-ray fat predictions using only the $A_{low}/A_{high}$ ratio are plotted against the fat reference results. The prediction error (expressed as the Root Mean Square Error of Prediction, RMSEP) is 14.7% in this case.

Figure 5:
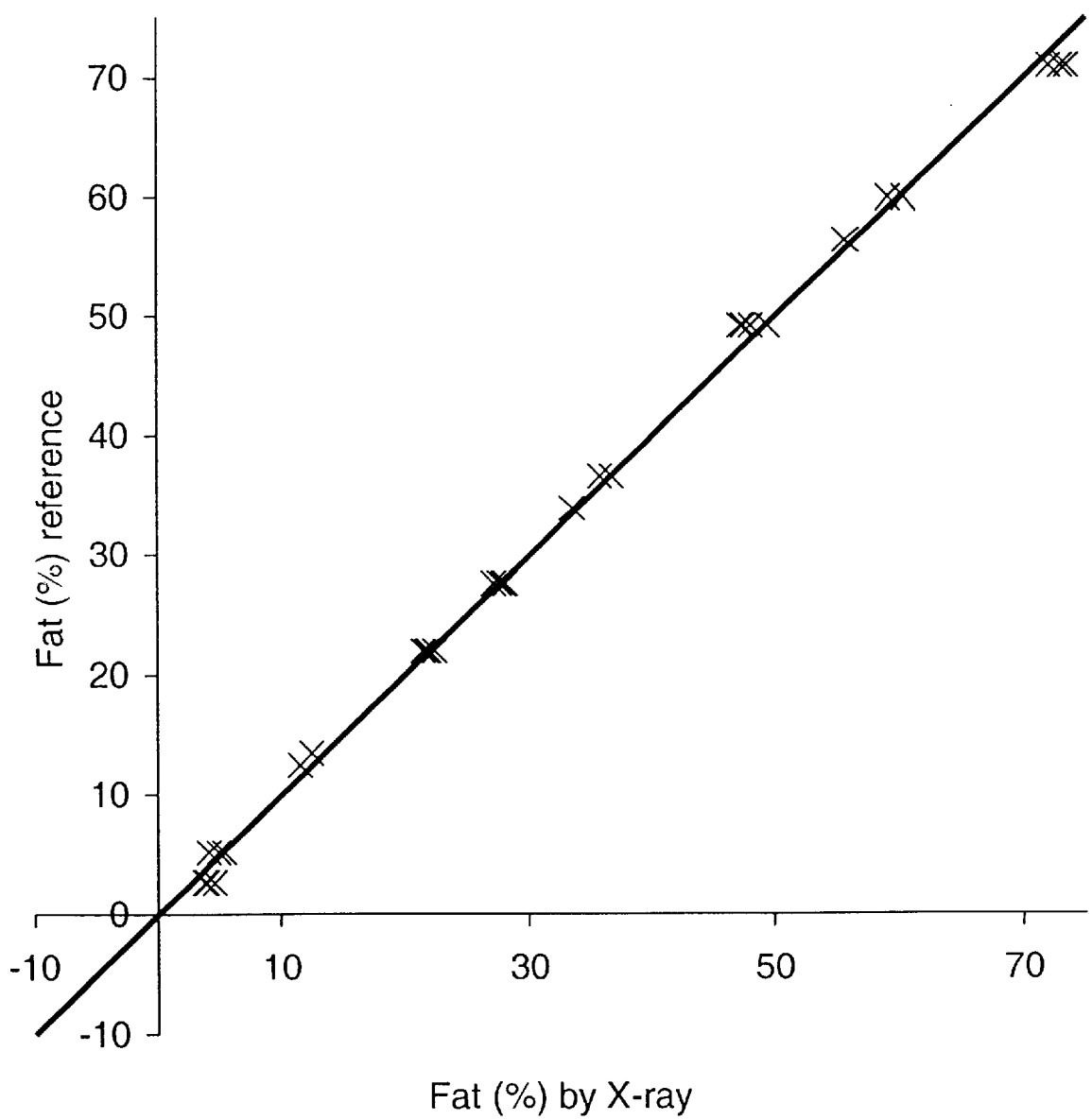
FIG. 5 shows cross-validated X-ray fat predictions versus reference fat content of 32 calibration samples when performing a PLS calibration with 5 PLS factors (based on 11 variables) against the reference fat content of the samples.

Using the method according to the invention, with e.g. 11 or more variables generated from the original two absorbences in combination with a PLS regression with 5 PLS-factors, the plot presented in FIG. 5 is obtained. In this case, the prediction error (RMSEP) is as low as 1.0%, thus showing the benefits of using the PLS method in combination with the new variables.

Figure 6:
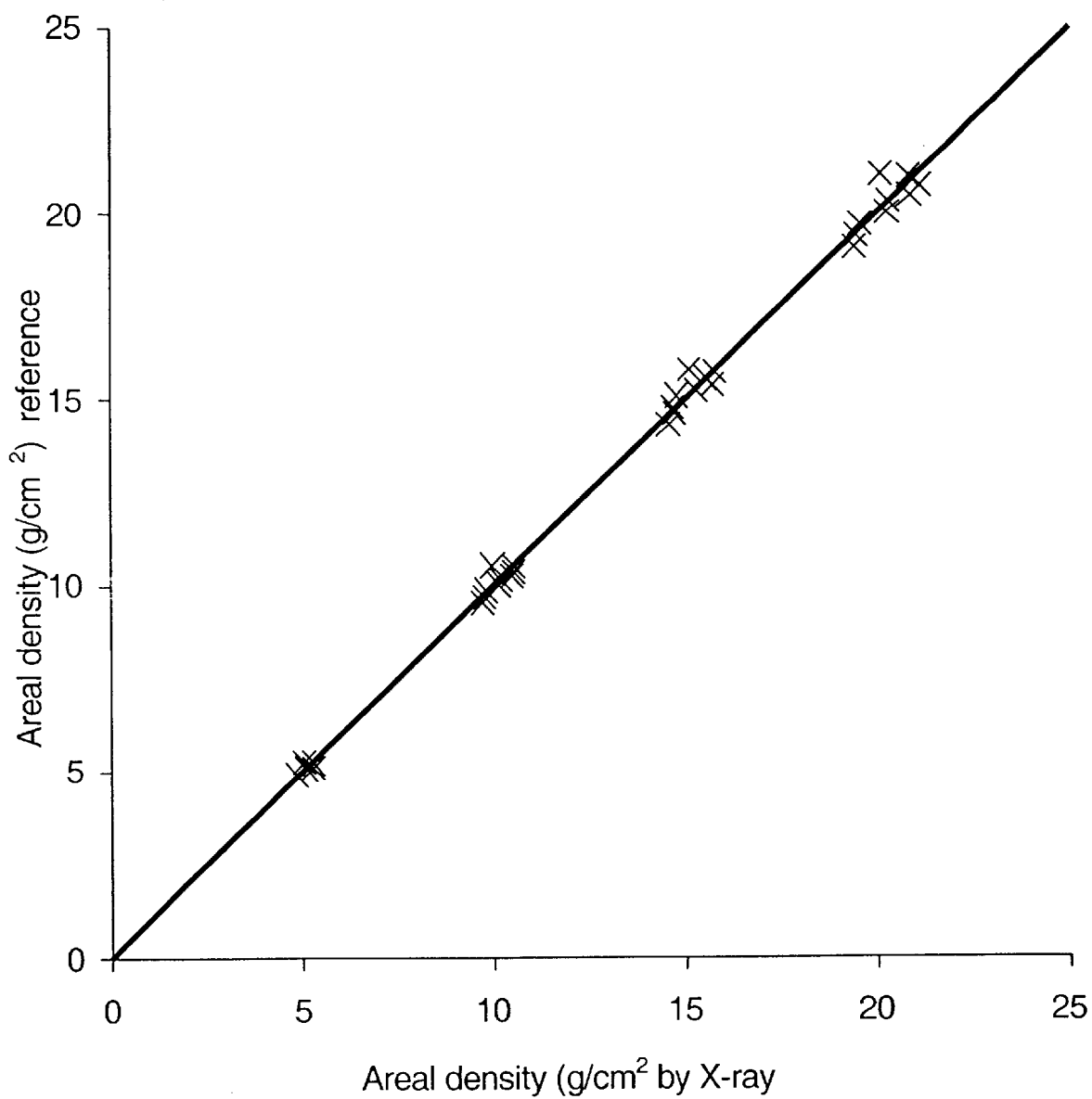
FIG. 6 shows cross-validated X-ray areal densities versus reference areal density of 32 calibration samples when performing a simple univariate regression of $A_{high}$ against the reference areal densities of the samples.
Figure 7:
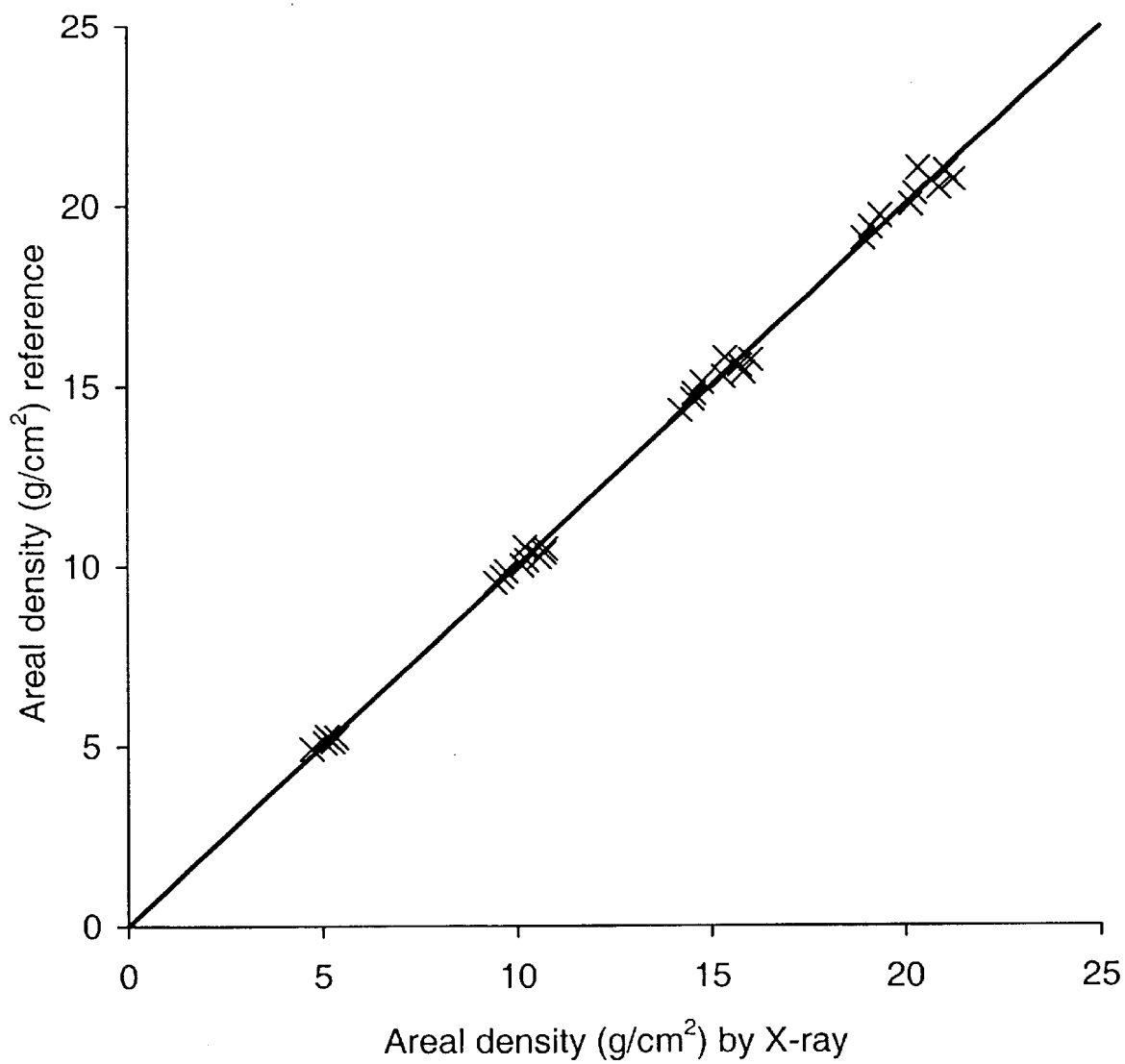
FIG. 7 shows cross-validated X-ray areal densities versus reference areal density of 32 calibration samples when performing a PLS calibration with 1 PLS factor (based on 2 variables) against the reference areal densities of the samples.

The method can also be applied for the determination of the areal density of the sample. According to the prior art the areal density is determined by correlating $A_{high}$ to the reference areal density. The result of such a calibration model is presented in FIG. 6, where the agreement between the areal density determined by X-ray and the reference results is very good. The prediction error (RMSEP) is 0.30 $g/cm^2$ in this case. When using the method according to the invention, i.e. using both measured absorbences, $A_{low}$ and $A_{high}$, in combination with a PLS regression with 1 factor, the result presented in FIG. 7, and a prediction error (RMSEP) of 0.28 $g/cm^2$, is obtained. This is only a slight improvement, but the use of two variables instead of one provides the user with a further advantage: the possibility of detecting incorrect measurements (e.g. if one of the two X-ray sources shows a sudden drop in intensity, or if a pixel is not responding). This is because discrepancies from the relationship between $A_{low}$ and $A_{high}$ can easily be detected by the PLS model. Such outlier detection is not possible if only one absorbance is used. This possibility is very relevant and advantageous when using CCD detector wherein a single pixel may deteriorate fairly abruptly.

The calibration models developed in this way can be used for future predictions of the fat content and areal density in a given point in an inhomogeneous meat sample as well as for determination of the mean fat content of a large meat sample.

Prediction of the Fat Content of an Unknown Meat Sample

The following example will demonstrate the use of the calibration models in practice where samples are inhomogeneous and of varying thickness. The purpose is to predict the mean fat content of the samples. Therefore the procedure involves the following steps as shown in FIG. 11:

1. Regular measuring of $I_{dark}$ and $I_{air}$, 102
2. Arranging a batch or stream of meat (or other food or feed product) on a conveyor passing through the X-ray apparatus, 104
3. Scanning the batch or stream by X-ray beams at two different energy levels, 106, 108,
4. Detecting signals representing a plurality of X-ray intensities, using the detectors 22, 24 in FIGS. 1, 2 110, 112
5. Recording data representing the detected signals 114.
6. Calculate $A_{low}$ and $A_{high}$ for all pixels 114, (optionally, a smoothing of the picture may be included.)
7. Co-ordinate (match) $A_{low}$ values and $A_{high}$ values 114, if necessary.
8. Calculate derived expressions $A_{low}^{n}*A_{high}^{m}$ 114.
9. Calculate the fat content (percentage) and preferably the areal density for all points (pixels) obtained from the scannings, using a fat calibration model generated as described above 116.
10. Multiply the fat content (percentage) and areal density at each point, in order to generate a "fat map" (in $g/cm^2$) of the batch or stream of food or feed 116.
11. Add all points in the "fat map" to give the total fat weight ($F_{total}$) 116.
12. Add all areal densities for the sample to give the total weight ($W_{total}$) 116.
13. Calculate the average fat content (percentage) as the ratio $F_{total}/W_{total}$ 116.

Optionally, two more steps may be included between step 6 and 7:

If the meat lumps are arranged in a container the data should be subjected to a correction for the absorption in the bottom of the container. Such correction is preferably made at the end of step 6, providing new corrected values of $A_{low}$ and $A_{high}$ for all pixels.

A further advantageous option is smoothing of the data, e.g. in the direction of the movement.

Further experience has proved that it can be advantageous to include a further data processing in step 9. In a presently preferred embodiment pixels having an areal density outside a specified interval are removed/deleted or at least disregarded in the following data processing, i.e. pixels for which the calculated areal density is extremely low or much too high, are rejected.

The present example shows the calculation of the fat content (percentage) for one row of 99 points only. This is done in order to make the presented plots simpler, and is easily generalised to be performed on a two-dimensional image of a meat product.

Example 1

Figure 8:
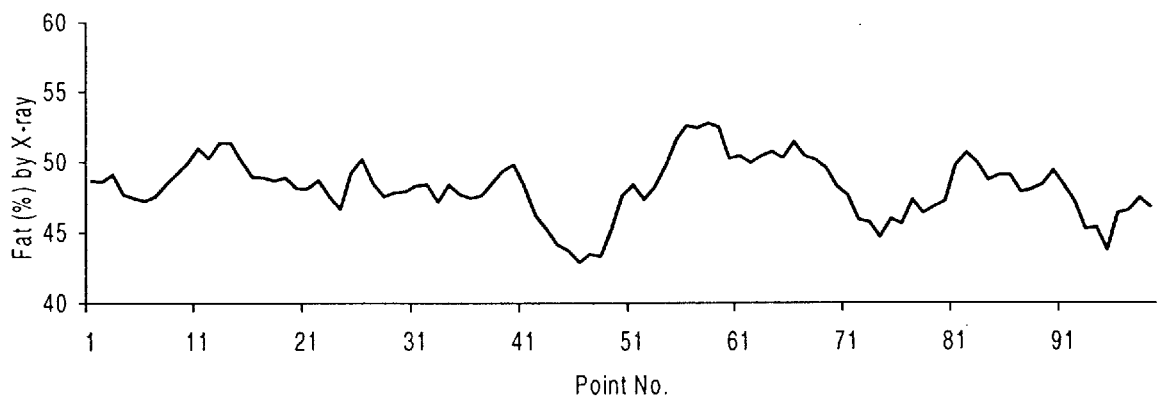
FIG. 8 shows Fat predicted by X-ray in 99 points of a meat sample.
Figure 9:
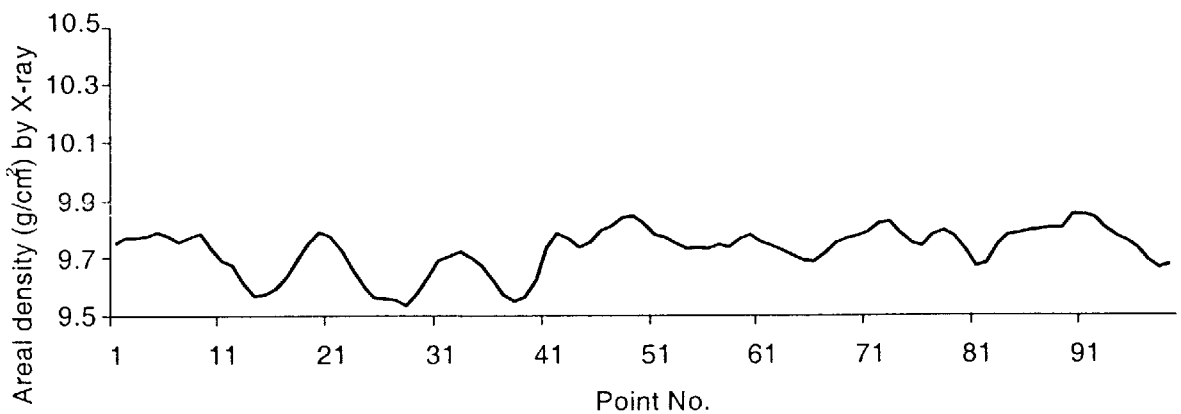
FIG. 9 shows Areal density predicted by X-ray in 99 points of a meat sample.
Figure 10:
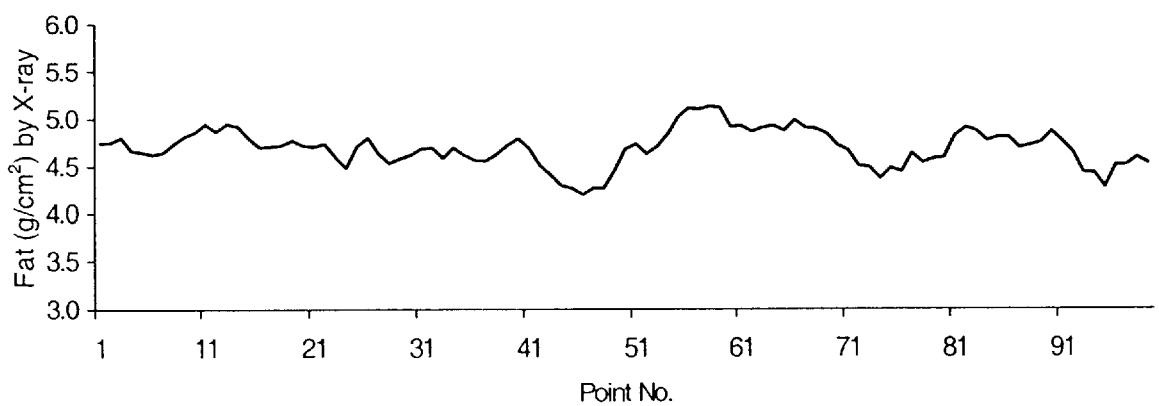
FIG. 10 shows Fat (in g/cm²) predicted by multiplication of the fat content (FIG. 8) by the areal density (FIG. 9) in 99 points of a meat sample.

A meat sample consisting of a cubic block (dimensions: 10×10×10 cm³) of minced pork meat was measured using the same X-ray equipment as was used for measuring the calibration samples. The first two steps of the prediction procedure are shown in FIG. 8 (predicted fat content (percentage) ), FIG. 9 (predicted areal density, step 9), and FIG. 10 (the "fat map", step 10). There is clearly a variation in both fat content and areal density over the sample, so the results from all sample points are needed in order to obtain an accurate estimate of the mean fat content of the sample.

The sum of all points in the "fat map" (step 11), $F_{total}$, equals 464 g/(99 pixels), and the total weight of the sample (step 12), $W_{total}$, is 963 g/(99 pixels). This, in turn, results in a predicted mean fat content of 464/963=48.2% (step 13), not far from the true fat content, which was determined later as 49.2% by a reference method.

Example 2

This example is an extension of the results stated above. The present example involves the prediction of the fat content of samples consisting of approximately 25 kg of meat in plastic containers.

Figure 12:
FIG. 12 shows a typical meat sample in a plastic container.

Ten samples of meat ranging from 11.5 to 84.6% fat were obtained from a meat processing plant. The amount of meat in each container ranged from 20 to 30 kg, the sample homogeneity ranging from ground meat to meat pieces of 5 kg each. A typical sample consisting of 36% fat trimmings arranged in a presently preferred container (dimensions: 70×40×17 cm³) is shown in FIG. 12.

Each of these ten samples were scanned by the instrument five times over a period of two days. Before each new scan the contents of the container was reorganised, i.e. the meat pieces were moved around without changing the total content of the container. This was done in order to check the repeatability of the measurement. A total of 50 X-ray scans, each consisting of a low and a high energy image of 306×1836 data points, were thus gathered. Two typical transmission images of a sample are shown in FIGS. 13 and 14.

All 50 scans were subjected to the prediction steps according to the invention, using a calibration model based on frozen meat samples. The calculated fat content and areal density for each individual pixel (step 9), as well as the "fat map" (step 10) for one sample are shown in FIGS. 16, 15, 17. The negative fat predictions are due to a relatively low signal-to-noise ratio on the individual pixels. This is, however, no problem, as the final averaging of the results reduces this error by orders of magnitude. From these images, the total fat content of the samples was calculated. The pooled repeatability standard deviation, $s_r$, for the five different scans of the same sample was 0.25%.

Figure 18:
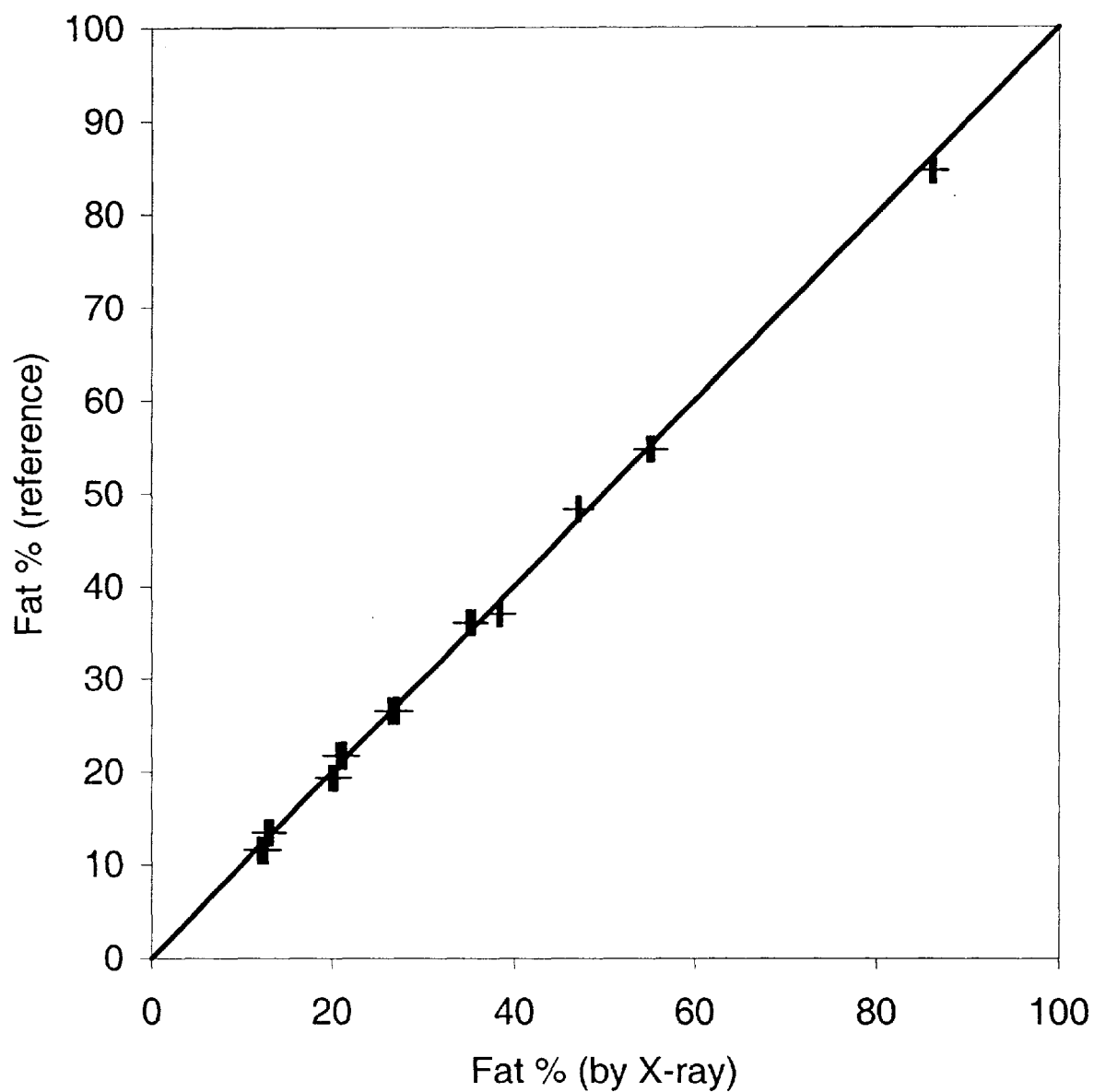
FIG. 18 shows a reference versus predicted plot for 50 scans.

After this experiment had been carried out the samples were homogenised and a number of subsamples were analysed by the reference method for fat in meat (Schmid-Bondzynski-Ratzlaff, SBR method). These reference results were compared to the predictions obtained above, resulting in an accuracy (Root Mean Square Error of Prediction, RMSEP) of 0.81%. The reference versus predicted plot for the 50 scans is shown in FIG. 18.

Example 3

To demonstrate the advantage of the method, in terms of its ability to significantly improve the accuracy of the fat determination, a further experiment was carried out. 45 frozen meat samples with fat contents ranging from 2.4 to 72.8% and areal densities ranging from 1 to 21 g/cm² were measured using the X-ray equipment. These samples were used for obtaining six different calibration models, using various combinations of the 11 variables based on $A_{low}$ and $A_{high}$ described above. Subsequently, these calibration models were tested on the same data set as used in Example 2, i.e. ten meat samples of 20 to 30 kg with fat contents ranging from 11.5 to 84.6% fat.

The six combinations of variables used for calibration models are shown in the table presented below, along with the resulting accuracies (RMSEP) on the calibration set (cross-validated) and the test set. Furthermore, the repeatability ($s_r$) on the test set was also calculated.

| calibration no. | $A_{low}$ | $A_{high}$ | $A_{low}^2$ | $A_{high}^2$ | $A_{low} \times A_{high}$ | $A_{low}^2 \times A_{high}$ | $A_{low} \times A_{high}^2$ | $A_{low}/A_{high}$ |
|---|---|---|---|---|---|---|---|---|
| 1 | + | + | + | + | + | | | |
| 2 | + | + | + | + | + | + | + | |
| 3 | + | + | + | + | + | + | + | + |
| 4 | + | + | + | + | + | + | + | + |
| 5 | | | | | + | + | + | + |
| 6 | | | | | | | | + |

-continued

| calibration no. | $A_{low}^2/A_{high}$ | $A_{low}/A_{high}^2$ | $(A_{low}/A_{high})^2$ | RMSEP (calibration) | RMSEP (test) | $S_r$ (test set) |
|---|---|---|---|---|---|---|
| 1 | | | | 9.43 | 1.52 | 0.41 |
| 2 | | | | 7.59 | 3.04 | 0.86 |
| 3 | | | | 0.93 | 1.09 | 0.26 |
| 4 | + | + | + | 0.79 | 0.81 | 0.25 |
| 5 | + | + | + | 2.30 | 1.17 | 0.23 |
| 6 | + | + | + | 3.36 | 3.31 | 0.26 |

From the results presented in the table the accuracy obtained when using only powers of $A_{low}$ and $A_{high}$ (calibration model 1) as well as products thereof (calibration model 2) are unacceptable if the method is to be used for process control within tight limits. If the $A_{low}/A_{high}$ ratio is added, combined with powers of $A_{low}$ and $A_{high}$ (calibration model 3), an acceptable accuracy is obtained. However, if powers of $A_{low}$ and $A_{high}$ are combined with $A_{low}/A_{high}$ and the more complex ratios (calibration model 4), even more accurate predictions result. It is also clear from calibration models 5 and 6 that of $A_{low}$ and $A_{high}$ and powers thereof are essential if the best possible accuracy is required.

In terms of the repeatability it is also clear that the $A_{low}/A_{high}$ ratio has a major influence on the difference between multiple determinations of the same sample.

The example presented above demonstrates the advantages in using higher order ratios for calibration of X-ray data against fat reference results. Only orders up to two were used in the present example, but ratios of higher orders may improve the result even further. For example, when using the ratios: $(A_{low}/A_{high})^3$; $(A_{low}/A_{high})^4$; $A_{low}^3/A_{high}$; $A_{low}^4/A_{high}$; $A_{low}^3/A_{high}^2$; $A_{low}^4/A_{high}^2$; $A_{low}^4/A_{high}^3$, an accuracy (RMSEP) of 0.67 is obtained on the calibration set.

The method may be applied to all kinds of meat, such as beef, veal, pork, buffalo, camel and lamb, game, such as rabbit, poultry, such as chicken, turkey, duck, goose and ostrich, and fish.

While a single particular embodiment of the invention has been mentioned, it will be understood, of course, that the invention is not limited thereto since many modifications may be made, such as using more than two X-ray sources or alternative arrangements such as arranging the sources below the conveyor or sidewards, and it is, therefore, contemplated to cover by the appended claims any such modifications as fall within the true spirit and scope of the invention.

What is claimed is:

1. A method of determining properties a medium of food or feed by use of dual X-ray absorptiometry, the medium being a raw material of food or feed, a product or intermediary product of food or feed, or a batch, sample or section of the same, the method comprising:
   scanning substantially all of the medium by X-ray beams having at least two energy levels, including a low level and a high level,
   detecting the X-ray beams having passed through the medium for a plurality of areas (pixels) of the medium,
   for each area calculating a value, $A_{low}$, representing the absorbance in the area of the medium at the low energy level,
   for each area calculating a value, $A_{high}$ representing the absorbance in the area of the medium at the high energy level,
   the method further comprises for each area generating a plurality of values being products of the type $A_{low}^n * A_{high}^m$ wherein n and m are positive and/or negative integers or zero, and
   predicting the properties of the medium in this area by applying a calibration model to the plurality of values, wherein the calibration model defines relations between the plurality of values and properties of the medium.

2. A Method according to claim 1, wherein the plurality of values including values $A_{low}^{n1}/A_{high}^{m1}$, wherein n1 and m1 are positive integers.

3. A method according to claim 1, wherein the plurality of values including the values $A_{low}$, $A_{high}$, $A_{low}^2$, $A_{high}^2$, and $A_{low}/A_{high}$.

4. A method according to claim 3, wherein the plurality of values including at least one of the values $A_{low}*A_{high}$, $A_{low}^2*A_{high}$, $A_{low}*A_{high}^2$, $A_{low}*A_{high}^4$ and $A_{low}^2*A_{high}^4$.

5. A method according to claim 3, wherein the plurality of values including at least one of the values $A_{low}^2/A_{high}$, $A_{low}/A_{high}^2$ and $A_{low}^2/A_{high}^2$.

6. A method according to claim 3, wherein the plurality of values including at least one of the values $A_{low}^3/A_{high}^2$, $A_{low}^4/A_{high}^2$, $1/A_{high}^4$, $A_{low}^4/A_{high}^3$, $A_{low}^3/A_{high}^4$ and $A_{low}^4/A_{high}^4$.

7. A method according to claim 1, wherein the calibration model being obtained by use of a regression method being included in the group comprising Principal Component Regression (PCR), Multiple Linear Regression (MLR), Partial Least Squares (PLS) regression, and Artificial Neural Networks (ANN).

8. A method according to claim 1, wherein the medium is arranged on a conveyor moving at substantially constant speed, and
   the at least two X-ray beams are fan-shaped, and the low level beam is detected by a first linear array, being dedicated to the detection of the low energy beam, and the high level beam is detected by a second linear array being dedicated to the detection of the high energy beam, each comprising a plurality of pixels.

9. An apparatus for the determination of properties of a medium, the medium comprising a raw material of food or feed, a product or intermediary product of food or feed, or a batch, sample or section of the same, the apparatus comprising:
   means for emitting at least two X-ray beams at two different energy levels,
   means for directing the at least two X-ray beams towards and through the medium,
   X-ray detection means covering a plurality of areas for detecting the two beams after passing through the medium,
   means for transferring and converting output signals from the detection means into digital data set for input to data processing means for receiving, storing and processing the at least two data sets representing X-ray images at the at least two different energy levels, the apparatus further comprising means for synchronising the at least two data sets and, the data processing means including means for calculating values representing the absorbances ($A_{low}$, $A_{high}$) in each area of the medium at the at least two energy levels, wherein the data processing means comprise means for generating a plurality of values being products of the type $A_{low}^{n} * A_{high}^{m}$ wherein n and m are positive and/or negative integers or zero, and means for predicting the properties of the medium in this area by applying a calibration model to the plurality of values, wherein the calibration defines relations between the plurality of values and properties of the medium.

10. An apparatus according to claim 9, comprising at least one low energy X-ray source arranged above the medium for providing a fan-shaped low energy beam substantially covering the width of medium and at least one high energy X-ray source arranged above the medium for providing a fan-shaped low energy beam covering the width of medium and a first X-ray detection means arranged to be exposed to the fan-shaped low energy beam and below the medium, a second X-ray detection means arranged to be exposed to the fan-shaped high energy beam and below the medium, and electronic means including the data processing means and communicating with the detectors and arranged to store and process data representing signals from the detection means and further comprising means for moving the medium relative to the X-ray beams or visa versa.

11. An apparatus according to claim 9, wherein that the data processing means include and/or communicate with means including data storage means comprising a calibration model prepared by use of multivariate calibration methods such as Artificial Neural Networks (ANN), or PCR, MLR or PLS regression analysis.

12. An apparatus according to claim 9, comprising at least two sources emitting X-rays of two different energy levels.

13. An apparatus according to claim 12, wherein the two energy levels comprising a low energy level in a range between 35 and 75 key, preferably between 45 and 70 key and most preferred about 62 key, and a high energy level in a range between about 60 and 140 key, preferably between 80 and 130 key and most preferred about 120 key.

14. An apparatus according to claim 9, comprising filter means located in each of the beams.

15. An apparatus according to claim 9, comprising one X-ray source and two filter means splitting the beam into two beams of X-rays at two different energy levels.

16. An apparatus according to claim 9, wherein the means for emitting at least two X-ray beams, the means for directing the at least two X-ray beams and the X-ray detection means are mutually fixed.

17. An apparatus according to claim 9, comprising means for emitting spatially separated fan-shaped beams.

18. An apparatus according to claim 9, wherein the means (12, 14) for emitting at least two X-ray beams, the means for directing the at least two X-ray beams and the X-ray detection means (22, 24) are mutually fixed.

19. An apparatus according to claims 9, comprising conveyor means arranged to carry container means, such as a tray or an open box, adapted to accommodate a random number of meat lumps of various sizes to be analysed, the conveyor means being arranged to let the container means pass the at least two fan-shaped X-ray beams.

20. An apparatus according to claim 19 comprising conveyor means wherein the conveyor belt is made from a material showing a low absorption of X-rays, and/or is split into two separate, spaced parts, the detector means being arranged in an open space between the two parts.

21. An apparatus according to claim 9, comprising conveyor means adapted to accommodate a continuous flow of meat lumps of various sizes to be analyzed, the conveyor means being arranged to let the meat lumps pass the at least two fan-shaped X-ray beams.

22. An apparatus according to claim 9, being arranged to perform the following steps:

scan at least a section of a medium by X-ray beams having at least two energy levels, store data representing at least two X ray images of the medium, calculate the fat content and/or a real density for all points (pixels) obtained from the scanning by use of multivariate calibration models generated in a previously performed calibration step, multiply the fat content and a real density at each point, in order to generate a "fat map" (in $g/cm^2$) of the sample, add all points in the "fat map" to give the total fat weight ($F_{total}$) of the sample, add all areal densities for the sample to give the total weight ($W_{total}$) of the sample, calculate the average fat content of the sample as the ratio $F_{total}/W_{total}$.

23. A method for calibration of an apparatus according to claim 9, comprising preparation of a plurality of calibration samples consisting of a specified medium comprising food or feed products, such as minced pork meat, of various well defined areal densities and properties, measurement of the plurality of calibration samples in the apparatus, thereby obtaining data representing two X-ray responses of each sample, each response comprising a plurality of pixels, and wherein the data of each pixel or the mean of a number of neighbouring pixels are processed to calculate the absorbances $A_{low}$ and $A_{high}$ in the medium above said pixel or pixels, generating a plurality of values of the type $A_{low}^{n} * A_{high}^{m}$, wherein n and m are positive and/or negative integers and/or zero, correlating—by use of multivariate calibration methods, such as Artificial Neural Networks (ANN) or 2CR, MLR or PLS regression—the data set for all/or a plurality of calibration samples to the properties determined by other means, such as a reference method,—in order to determine a number of calibration coefficients, providing a calibration comprising the number of determined calibration coefficients.

24. A method according to claim 23, wherein all calibration samples are prepared in such a manner that they are homogeneous and of fixed a real densities, and further by averaging each of the values over all pixels at least in a defined portion of the images.

25. A method of predicting the fat content of meat by use of dual X-ray absorptiometry, using a calibration model obtained by a method according to claim 23.

26. An apparatus according to claim 23, comprising a calibration model determined by a method comprising preparation of a plurality of calibration samples consisting of a specified medium comprising food or feed products, such as minced pork meat, of various well defined areal densities and properties, measurement of the plurality of calibration samples in the apparatus, thereby obtaining data representing two X-ray responses of each sample, each response comprising a plurality of pixels, and wherein the data of each pixel or the mean of a number of neighbouring pixels are processed to calculate the absorbances $A_{low}$ and $A_{high}$ in the medium above said pixel or pixels, generating a plurality of values of the type $A_{low}{}^{n}*A_{high}{}^{m}$, wherein n and m are positive and/or negative integers and/or zero, correlating—by use of multivariate calibration methods, such as Artificial Neural Networks (ANN) or PCR, MLR or PLS regression—the data set for all/or a plurality of calibration samples to the properties determined by other means, such as a reference method,—in order to determine a number of calibration coefficients, providing a calibration comprising the number of determined calibration coefficients.

27. An apparatus according to claim 26, wherein all calibration samples are prepared in such a manner that they are homogeneous and of fixed areal densities, and further by averaging each of the values over all pixels at least in a defined portion of the images.

* * * * *

UNITED STATES PATENT AND TRADEMARK OFFICE
CERTIFICATE OF CORRECTION

PATENT NO. : 6,600,805 B2
DATED : July 29, 2003
INVENTOR(S) : Hansen, Per Waaben It is certified that error appears in the above-identified patent and that said Letters Patent is hereby corrected as shown below:

Column 13,
Line 50, after "properties" insert -- of --.

Column 15,
Line 36, delete "that".
Lines 45 and 48, change "key" to -- keV -- (both occurrences);
Lines 46 and 47, change "key" to -- keV --.
Lines 61-64, change "means (12,14) for emitting at least two X-ray beams, the means for directing the at least two X-ray beams and the X-ray detection means (22, 24) are mutually fixed" to read -- detection means (22,24) are covered by a scintillating layer, e.g. cadmium telluride, mercury iodide, and/or gadolinium oxysulphide --.

Column 16,
Line 51, change "2CR" to -- PCR --.
Line 60, change "a real" to -- areal --.

Signed and Sealed this

Twentieth Day of July, 2004

JON W. DUDAS
*Acting Director of the United States Patent and Trademark Office*